US012685565B2

(12) United States Patent
Schmidt et al.

(10) Patent No.: US 12,685,565 B2
(45) Date of Patent: Jul. 21, 2026

(54) SURGICAL INSTRUMENTS, GUIDES, AND METHODS OF USE

(71) Applicant: Paragon 28, Inc., Englewood, CO (US)

(72) Inventors: Michael Schmidt, Greenwood Village, CO (US); Richard David Hunt, Arvada, CO (US); Albert Dacosta, Lone Tree, CO (US)

(73) Assignee: Paragon 28, Inc., Englewood, CO (US)

( * ) Notice: Subject to any disclaimer, the term of this patent is extended or adjusted under 35 U.S.C. 154(b) by 649 days.

(21) Appl. No.: 18/160,789

(22) Filed: Jan. 27, 2023

(65) Prior Publication Data

US 2023/0240720 A1 Aug. 3, 2023

Related U.S. Application Data

(60) Provisional application No. 63/304,144, filed on Jan. 28, 2022.

(51) Int. Cl.
  *A61B 17/66* (2006.01)
  *A61B 17/17* (2006.01)
(52) U.S. Cl.
  CPC .......... *A61B 17/66* (2013.01); *A61B 17/1775* (2016.11)
(58) Field of Classification Search
  CPC ..... A61B 17/66; A61B 17/17; A61B 17/1775; A61B 17/88; A61B 17/8866
  See application file for complete search history.

(56) References Cited

U.S. PATENT DOCUMENTS

| | | | |
|---|---|---|---|
| 2012/0101502 A1 | 4/2012 | Kartalian | |
| 2014/0031882 A1 | 1/2014 | Schmuck | |
| 2017/0113330 A1 | 4/2017 | Williams | |
| 2017/0209192 A1 | 7/2017 | Krauss | |
| 2018/0064459 A1 | 3/2018 | Alshemari | |
| 2020/0289182 A1 | 9/2020 | Chang | |
| 2020/0375644 A1 | 12/2020 | Smith | |
| 2022/0175436 A1 * | 6/2022 | Gil | A61B 17/8866 |
| 2022/0401139 A1 * | 12/2022 | Korman | A61B 17/8866 |

(Continued)

FOREIGN PATENT DOCUMENTS

| | | |
|---|---|---|
| CN | 112472214 | 3/2021 |
| EP | 0792621 | 9/1997 |

(Continued)

*Primary Examiner* — Christopher J Beccia
(74) *Attorney, Agent, or Firm* — Heslin Rothenberg Farley & Mesiti P.C.; Jacquelyn A. Graff, Esq.

(57) ABSTRACT

The present disclosure relates to an alignment system. The alignment system includes a clamp portion including a curved member configured to contact a medial portion of a first metatarsal of a patient, and a retention element configured to releasably couple with a second metatarsal of the patient. The alignment system also includes an alignment portion releasably coupled with the clamp portion and including an alignment bar and an extension coupled with the alignment bar and configured to releasably couple with a guide arm. The retention element includes a shaft and a pair of protrusions extending from a distal-most point of the shaft, with the pair of protrusions extend substantially parallel to one another. Also disclosed is a method of coupling the alignment system to the anatomy of a patient, specifically to two bones in the foot of the patient.

16 Claims, 6 Drawing Sheets

(56) References Cited

U.S. PATENT DOCUMENTS

2023/0149031 A1* 5/2023 Woodard ........... A61B 17/8866
606/87
2024/0032955 A1 2/2024 Schmidt

FOREIGN PATENT DOCUMENTS

WO 2011037885 3/2011
WO 2020186112 9/2020

* cited by examiner

SURGICAL INSTRUMENTS, GUIDES, AND METHODS OF USE

CROSS-RELATED APPLICATION

This application perfects U.S. Provisional Application No. 63/304,144 filed Jan. 28, 2022, titled SURGICAL INSTRUMENTS, GUIDES, AND METHODS OF USE, the contents of which is incorporated herein by reference.

TECHNICAL FIELD

The present disclosure relates to surgical instruments, guides, and methods of use to be implemented in surgical procedures. The present disclosure relates to podiatric and orthopedic surgical instruments, guides, and methodology to be implemented in various surgical procedures of the foot and/or ankle, for example arthrodesis. More specifically, but not exclusively, the present disclosure relates to surgical instruments, guides to be implemented in conjunction with the instruments (as well as other components, for example implants, devices, systems, assemblies, etc.) and methods of use for performing arthrodesis procedures of the Lapidus joint.

BACKGROUND OF THE INVENTION

Many currently available surgical instruments and guides, as well as surgical methodology, do not completely address the needs of patients. Additionally, many currently available surgical instruments, guides, and methodology fail to account for properties of joint anatomy and accordingly can decrease favorability of the outcome for the patient.

SUMMARY OF THE INVENTION

The present disclosure is directed toward surgical guides for implementation in conjunction with implants, instruments, and methods directed to arthrodesis and other similar procedures.

A first aspect of the present disclosure is an alignment system. The alignment system includes a clamp portion including a curved member configured to contact a medial portion of a first metatarsal of a patient, and a retention element configured to releasably couple with a second metatarsal of the patient. The alignment system also includes an alignment portion releasably coupled with the clamp portion and including an alignment bar and an extension coupled with the alignment bar and configured to releasably couple with a guide arm.

According to one aspect of the present disclosure, the retention element is arranged substantially opposite the clamp portion from the curved member.

According to one aspect of the present disclosure, the retention element includes a shaft and a pair of projections extending from the shaft and terminating at a distal portion of the retention element.

According to one aspect of the present disclosure, the clamp portion includes a coupling member having a shaft portion with a threading disposed on at least a portion of an outer surface thereof, and a knob disposed opposite the coupling member from a distal-most portion of the shaft portion.

According to one aspect of the present disclosure, the curved member includes a coupling portion configured to threadably and translatably couple with the shaft portion of the coupling member.

According to one aspect of the present disclosure, the clamp portion includes a connecting member having a first opening configured to receive at least a portion of the shaft of the coupling member therein, and a second opening configured to receive at least a portion of the shaft of the retention element therein.

According to one aspect of the present disclosure, the first opening includes a first longitudinal axis, and the second opening includes a second longitudinal axis, wherein the first and second longitudinal axes are positioned in planes substantially orthogonal to one another.

According to one aspect of the present disclosure, actuation of the knob of the coupling member is configured to translate the curved member along a length of the shaft portion of the coupling member.

According to one aspect of the present disclosure, translation of the curved member along the length of the shaft of the coupling member is configured to increase or decrease a distance between the retention element and the curved member.

According to one aspect of the present disclosure, the alignment system also includes an alignment portion having an alignment bar with a first opening configured to receive at least a portion of the shaft of the retention element therethrough.

According to one aspect of the present disclosure, the alignment bar includes an elongated opening and a slider disposed within and translatable along a length of the elongated opening, wherein the slider includes a bore extending therethrough.

According to one aspect of the present disclosure, the alignment bar also includes a guide portion with a shaft protruding from a lateral portion thereof and configured to be received at least partially through the bore of the slider.

A second aspect of the present disclosure is directed toward a retention element. The retention element includes a shaft and a pair of protrusions extending from a distal-most point of the shaft, wherein the pair of protrusions extend substantially parallel to one another.

According to one aspect of the present disclosure, the retention element includes a threading disposed on at least a portion of the shaft.

According to one aspect of the present disclosure, each of the projections of the retention element include a lobe disposed on an inner portion thereof and extending into a space between each of the projections.

According to one aspect of the present disclosure, each of the projections include a textured surface disposed on an inner portion thereof and positioned between the lobe and the termination of the projection.

According to one aspect of the present disclosure, each of the pair of projections define a space therebetween configured to receive at least a portion of a bony anatomy of a patient.

According to one aspect of the present disclosure, each of the pair of projections are configured to be flexible such that a force applied simultaneously to an outer surface of each of the projections decreases the space between the projections.

According to one aspect of the present disclosure, each of the projections are integral with the shaft.

A third aspect of the present disclosure is directed toward a method of coupling an alignment system with the anatomy of a patient. The method includes inserting a retention element having a pair of projections over a first bony anatomy of a patient such that the first bony anatomy is disposed at least partially between the projections, and releasably coupling a connecting member with the retention element such that at least a portion of a shaft of the retention element is received through a first opening of the connecting member. The method also includes releasably coupling the connecting member with a coupling member such that a shaft of the coupling member is received through a second opening of the connecting member, and releasably coupling a curved member with the shaft portion of the coupling member such that at least a portion of the shaft of the coupling member is received through a third opening of the curved member. Further, the method includes actuating the coupling member to adjust the space between the curved member and the retention element such that the curved member is positioned adjacent a second bony anatomy of the patient.

BRIEF DESCRIPTION OF THE DRAWINGS

The accompanying drawings, which are incorporated in and constitute a part of the specification, illustrate embodiments of the inventions and together with the detailed description herein, serve to explain the principles of the inventions. It is emphasized that, in accordance with the standard practice in the industry, various features may or may not be drawn to scale. In fact, the dimensions of the various features may be arbitrarily increased or reduced for clarity of discussion. The drawings are only for purposes of illustrating embodiments of inventions of the disclosure and are not to be construed as limiting the inventions.

DETAILED DESCRIPTION OF THE INVENTION

Figure 1:
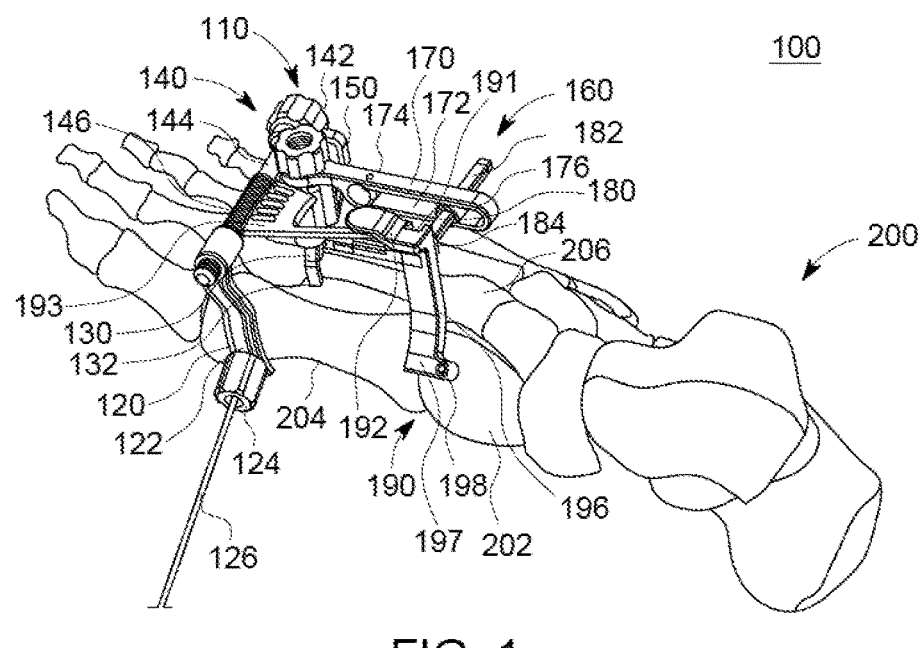
FIG. 1 is a top medial perspective view of an exemplary system for implementation in performing a surgical procedure shown adjacent to a corresponding portion of the anatomy, in accordance with the present disclosure.
Figure 2:
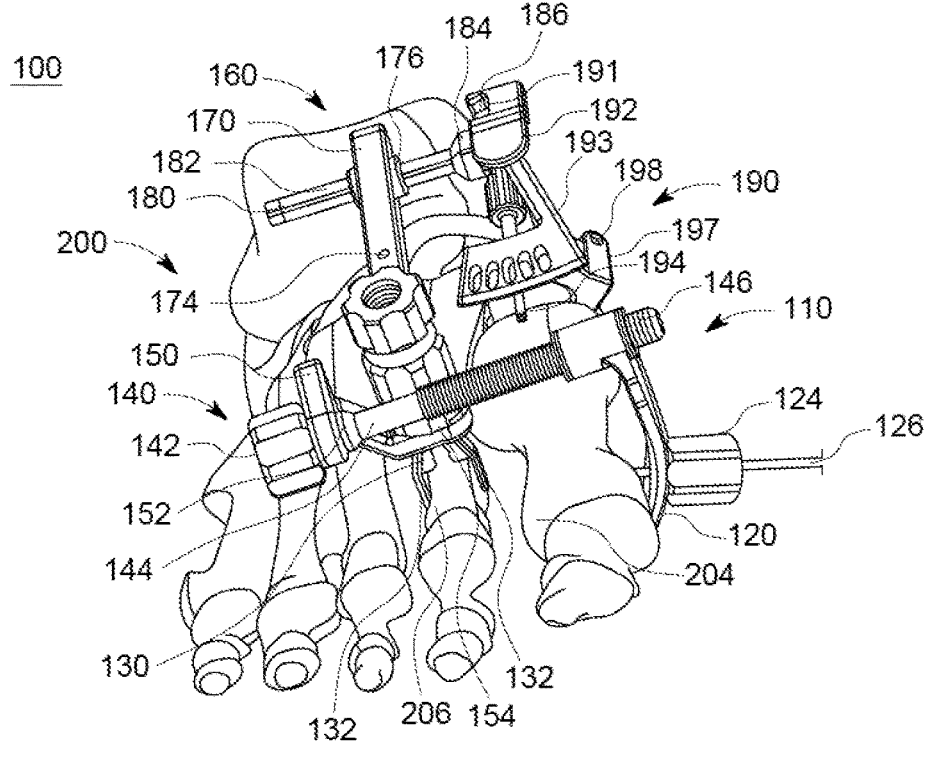
FIG. 2 is a front perspective view of the exemplary system of FIG. 1, in accordance with the present disclosure.
Figure 3:
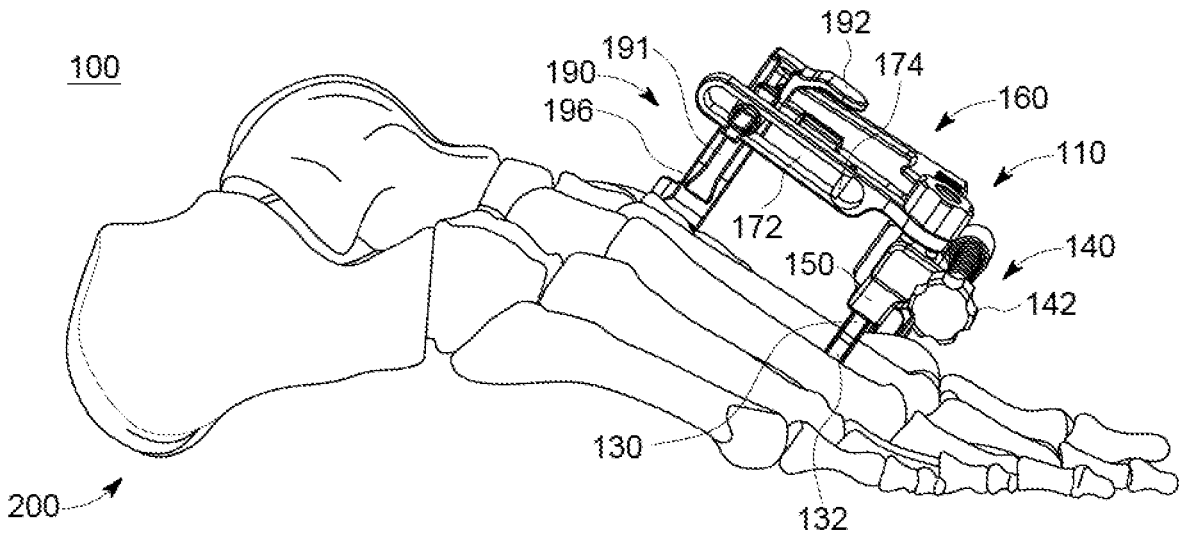
FIG. 3 is lateral perspective view of the exemplary system of FIG. 1, in accordance with the present disclosure.
Figure 4:
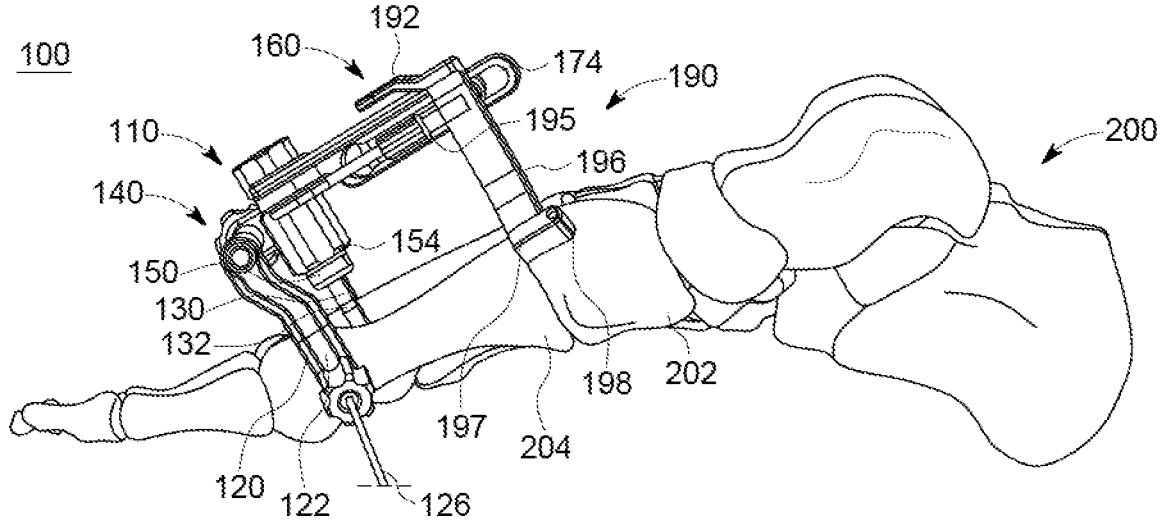
FIG. 4 is a medial view of the exemplary system of FIG. 1, in accordance with the present disclosure.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation, and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation, and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation, and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation, and methods, and the aspects, components, features and the like thereof, described herein with respect to the right foot may be mirrored so that they likewise function with the left foot. Further, the implants, devices, instrumentation, and methods, and the aspects, components, features and the like thereof, disclosed herein are described with respect to the foot for brevity purposes, but it should be understood that the implants, devices, instrumentation, and methods may be used with other bones of the body having similar structures.

The instruments, implants, systems, assemblies, and related methods for maintaining, correcting, and/or resurfacing joint surfaces of the present disclosure may be similar to, such as include at least one feature or aspect of, the implants, systems, assemblies and related methods disclosed in International PCT Application No. PCT/US2018/20046, filed on Feb. 27, 2018, and entitled Intramedullary Nail Alignment Guides, Fixation Guides, Devices, Systems, and Methods of Use; International PCT Application No. PCT/US2018/64368, filed on Dec. 17, 2018, and entitled Alignment Guides, Cut Guides, Systems and Methods of Use and Assembly; International PCT Application No. PCT/US2019/041146, filed on Jul. 10, 2019, and entitled Guides, Instruments, Systems and Methods of Use; and/or International PCT Application No. PCT/US2014/27086, filed on Mar. 14, 2014, and entitled Intramedullary Nail Fixation Guides, Devices, and Methods of Use; and/or U.S. Pat. No. 9,980,760 filed on Nov. 19, 2014, and entitled Step Off Bone Plates, Systems, and Methods of Use; and/or U.S. Pat. No. D720,456 filed on Jul. 26, 2012 and entitled Lapidus Bone Wedge; and/or U.S. Pat. No. D765,844 filed on Oct. 23, 2014 and entitled Bone Plate; and/or U.S. Pat. No. D695,402 filed on Dec. 10, 2013 and entitled Lapidus Cut Guide; and/or U.S. Pat. No. D904,2016 filed on Nov. 22, 2017 and entitled Intramedullary Fastener; and/or U.S. Pat. No. D865,173 filed on Jul. 9, 2018 and entitled Cut Guide; and/or U.S. patent application Ser. No. 29/686,941 filed on Apr. 9, 2019 and entitled Cut Guide; and/or U.S. Pat. No. D904,609 filed on Apr. 9, 2019 and entitled Cut Guide; and/or U.S. Pat. No. D9042010 filed on Apr. 9, 2019 and entitled Cut Guide; which are hereby incorporated herein by reference in their entireties. Similarly, the instruments, implants, systems, assemblies, and related methods for maintaining, correcting, and/or resurfacing joint surfaces of the present disclosure may include one or more instruments (e.g., one or more insertion and/or implantation instruments) disclosed in U.S. Provisional Application No. 63/173,043, filed Apr. 9, 2021 and entitled Surgical Instruments, Guides, and Methods of Use; and/or International PCT Application No. PCT/US2018/20046, filed on Feb. 27, 2018, and entitled Intramedullary Nail Alignment Guides, Fixation Guides, Devices, Systems, and Methods of Use; and/or International PCT Application No. PCT/US2018/64368, filed on Dec. 17, 2018, and entitled Alignment Guides, Cut Guides, Systems and Methods of Use and Assembly; and/or International PCT Application No. PCT/US2019/041146, filed on Jul. 10, 2019, and entitled Guides, Instruments, Systems and Methods of Use; and/or International PCT Application No. PCT/US2014/27086, filed on Mar. 14, 2014, and entitled Intramedullary Nail Fixation Guides, Devices, and Methods of Use; and/or U.S. Pat. No. 9,980,760 filed on Nov. 19, 2014, and entitled Step Off Bone Plates, Systems, and Methods of Use; and/or U.S. Pat. No. D720,456 filed on Jul. 26, 2012 and entitled Lapidus Bone Wedge; and/or U.S. Pat. No. D765,844 filed on Oct. 23, 2014 and entitled Bone Plate; and/or U.S. Pat. No. D695,402 filed on Dec. 10, 2013 and entitled Lapidus Cut Guide; and/or U.S. Pat. No. D904,2016 filed on Nov. 22, 2017 and entitled Intramedullary Fastener; and/or U.S. Pat. No. D865,173 filed on Jul. 9, 2018 and entitled Cut Guide; and/or U.S. patent application Ser. No. 29/686,941 filed on Apr. 9, 2019 and entitled Cut Guide; and/or U.S. Pat. No. D904,609 filed on Apr. 9, 2019 and entitled Cut Guide; and/or U.S. Pat. No. D9042010 filed on Apr. 9, 2019 and entitled Cut Guide; and/or U.S. Provisional Patent Application No. 63/262,845 filed on Oct. 21, 2021 and entitled Surgical Instruments, Guides, and Methods of Use, which are hereby incorporated herein by reference in their entireties.

Procedures to address deformities such as bunions and anatomical structures of and around the Lapidus joint frequently require the positioning/repositioning and/or rotation/derotation of the first metatarsal. Referred to herein as the "Lapidus" joint, this joint may also be known and referred to as the first tarsometatarsal joint. It is common for a procedure of the Lapidus joint (e.g., fusion/arthrodesis) to require that the first metatarsal be manipulated by applying one or more forces to the first metatarsal. In some procedures, this manipulation is necessary before any cutting and/or preparation and subsequent fusion of the Lapidus joint can take place. In evaluating a Lapidus joint deformity, two different criteria are typically analyzed for correction. One of these criteria is the intramedullary angle formed between the longitudinal axes of the first metatarsal and the second metatarsal. Bunion deformities and other conditions of the Lapidus joint often include the first metatarsal shifting medially from a normal anatomical position, thus increasing the IM angle between the first and second metatarsals from what can be considered an anatomically correct range of angle measures. Rotation of the first metatarsal is also analyzed, as bunion deformities and other conditions of the Lapidus joint commonly include a first metatarsal that has rotated substantially in the frontal plane in a substantially clockwise direction (when viewed from an anterior to posterior direction). Commonly, a Lapidus joint procedure such as those mentioned previously requires manipulation of the first metatarsal so as to: a) correct (e.g., decrease) the IM angle between the first and second metatarsals by applying a substantially lateral force to the first metatarsal; and/or b) derotate the first metatarsal which as rotated from a normal anatomical position by applying a rotational force in a substantially counterclockwise direction when the first metatarsal is viewed in an anterior to posterior direction.

Figure 5:
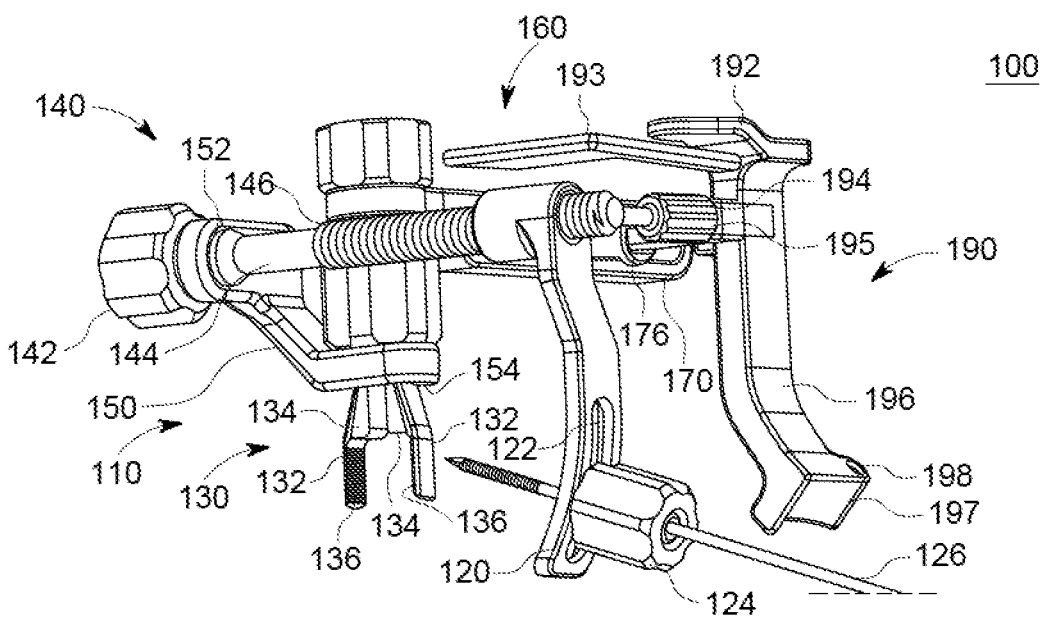
FIG. 5 is a front-medial perspective view of the exemplary system of FIG. 1, in accordance with the present disclosure.
Figure 6:
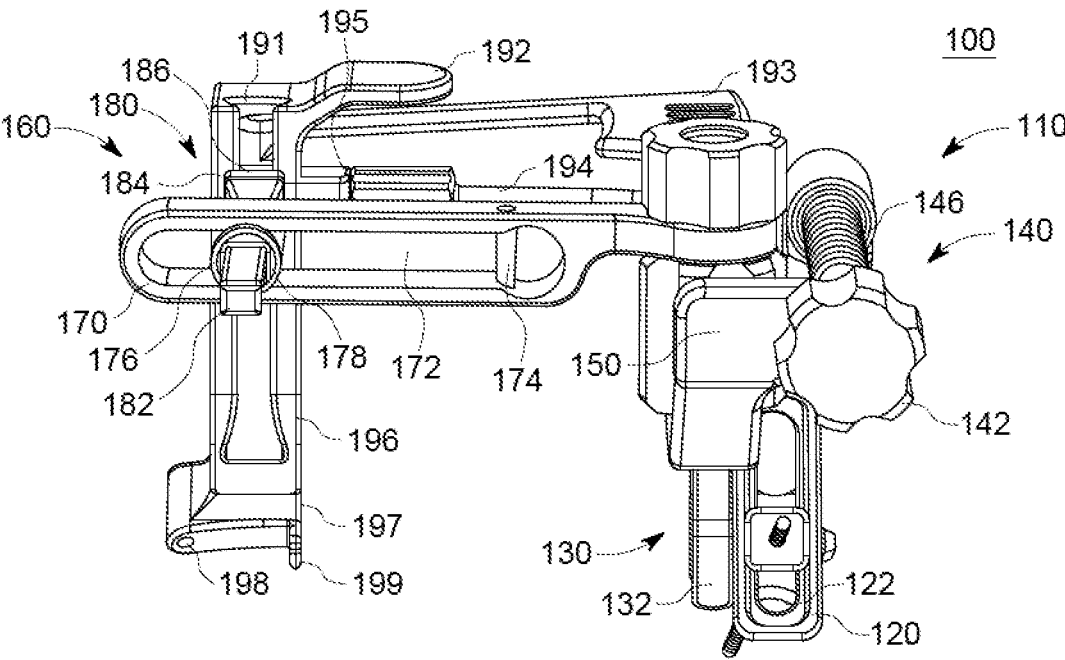
FIG. 6 is a lateral perspective view of the exemplary system of FIG. 1, in accordance with the present disclosure.
Figure 7:
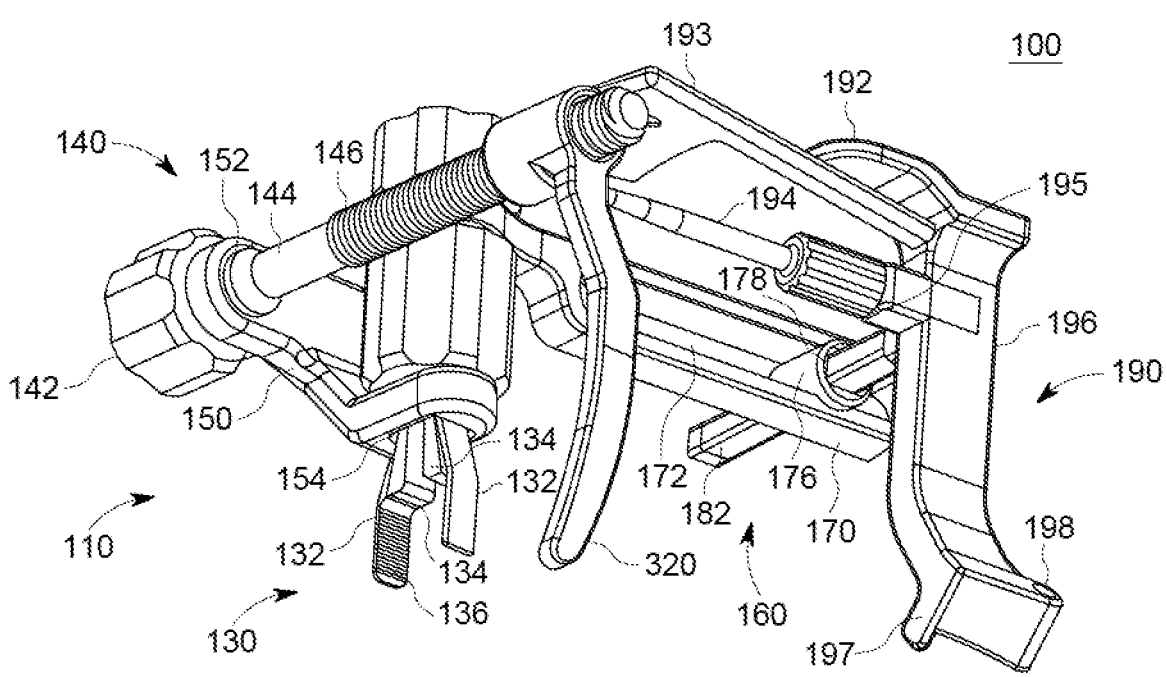
FIG. 7 is a front-medial perspective view of an alternative system of the exemplary system of FIG. 1, in accordance with the present disclosure.

Referring to the drawings, wherein like reference numerals are used to indicate like or analogous components throughout the several views, and with particular reference to FIGS. 1-6, there is illustrated an exemplary embodiment of a clamp system 100 for implementation in performing a procedure on one or more anatomical structures of the foot (for example, procedures of the Lapidus joint such as arthrodesis or other similar fusion procedures). In some aspects, the system 100 may be manipulated such that one or more components of the system 100 contact one or more anatomical structures of the foot and, when force is applied to the one or more components of the system 100 by a physician, at least one of said anatomical structures is selectively repositioned by the physician (e.g., in preparation for arthrodesis). The system 100, as shown and described herein, is shown in FIGS. 1-7, where FIGS. 1-4 show a first embodiment of the system adjacent an exemplary foot 200 of a patient, FIGS. 5-7 show the first embodiment of the system independent of any anatomy. It should be understood that the system 100 may include one or more components in addition to those shown and described herein (e.g., cutting instruments, saws, scalpels, forceps, retractors, etc.) and accordingly, the system 100 and/or any components thereof may be implemented in conjunction with the method described herein (where the method may also be implemented with components other than those shown and described herein).

The system 100 is shown to include a clamp 110 (e.g., first portion, handle, etc.) configured to aid a physician in determining, aligning/realigning, correcting, positioning/repositioning, rotating/derotating, or otherwise manipulating one or more anatomical structures of the foot relative to other anatomical structures of the foot in accordance with the present disclosure. As shown and described herein, the clamp 110 is configured to releasably couple (via one or more components shown and described subsequently herein) with structures of the foot 200 as shown and described in FIGS. 1-4 including a medial cuneiform (shown as reference numeral 202), a first metatarsal (shown as reference numeral 204), and a second metatarsal (shown as reference numeral 206) so as to manipulate a Lapidus joint positioned between the medial cuneiform 204 and the first metatarsal 204. In some aspects, the clamp 110 may be implemented on distal portions of the first and second metatarsals 204, 206, but may also be implemented elsewhere about the first and second metatarsals 204, 206. The clamp 110 (and components thereof) is configured to facilitate the correction of the IM (intramedullary) angle formed between a first extended longitudinal axis of the first metatarsal 204 and a second extended longitudinal axis of the second metatarsal 206. Further, the clamp 110 is configured to facilitate derotation (e.g., rotation opposite that which caused a bunion or other deformity) of the first metatarsal 204 relative to the second metatarsal 206. Correction of IM angle and/or derotation of the first metatarsal 204 relative to the second metatarsal 206 may be performed by a physician in a procedure to address a deformity at or near the Lapidus joint (e.g., bunion, arthrodesis of Lapidus joint, etc.).

The clamp 110 is shown to include a curved member 120 and a retention element 130 (e.g., a metatarsal grip, etc.) arranged substantially opposite a coupling member 140. The curved member 120 is shown to include a coupling portion at a first (e.g., proximal) end, wherein said coupling portion is configured to receive at least a portion of a shaft 144 of the coupling member 140. As shown, the shaft 144 includes a threading 146 disposed along at least a portion of the length thereof. The coupling portion of the curved member 120 is shown to include a substantially cylindrical geometry with an open center portion extending therethrough about a central longitudinal axis. In some aspects, the inner surface of said open center portion may include a threading complimentary to the threading 146 of the shaft 144 of the coupling member 140 such that the curved member 120 may releasably (and, for example, rotatably, threadedly, etc.) couple with at least a portion of the coupling member 140. The curved member 120 is shown to extend in a distal direction (e.g., opposite the coupling portion) in a curved geometry, where said curved geometry (which may include one or more radius/radii of curvature) is configured to contact an outer surface of the first metatarsal 204 (on a lateral side thereof). As shown, the curved member 120 has a substantially concave geometry on a first (e.g., medial-facing, as shown) side, and a substantially convex geometry on a second (e.g., lateral-facing, as shown) side. In some aspects, only a portion of the curved member 120 may contact the surface of the first metatarsal 204 at a time, with said curvature of the curved member 120 configured to facilitate smooth movement of the first metatarsal 204 along the curvature when manipulated by a physician.

The curved member 120 is shown to include a slot 122 disposed in a central portion of the curved member 120, for example between the coupling portion at a proximal-most end and a distal-most end opposite the curved member 120 from the proximal-most end. As shown, the slot 122 includes a curved geometry the same as and/or similar to that of the curved member 120. Further, the slot 122 has a substantially elongated shape which is defined by substantially parallel edges forming the longest dimensions of the slot 122 and substantially rounded end portions forming the shortest dimensions of the slot 122. The curved member 120 is further shown to include an actuator 124, wherein the actuator 124 is disposed at least partially within the slot 122 of the curved member 120. For example, and as shown in FIGS. 1-7, the actuator 124 may include a first portion disposed on a lateral side of the curved member 120, and intermediate portion disposed at least partially within the slot 122, and a second portion disposed on a medial side of the curved member 120. Further to the previous example, the intermediate portion may include a lateral geometry that is configured to be accommodated within the slot 122, and with said lateral geometry lesser than that of the first portion and the second portion such that the actuator 124 is retained with the intermediate portion disposed within the slot 122. Accordingly, the actuator 124 may be releasably coupled with the curved member 120 via the slot 122 such that the actuator 124 may move within a range of motion defined by the intermediate portion thereof contacting the curved end portions of the slot 122.

The actuator 124 as shown may include a bore centered concentrically about a longitudinal axis extending therethrough from the aforementioned second portion, through the intermediate portion disposed within the slot 122, and through the first portion such that fluid communication may be established through the actuator 124. The bore may be cylindrical in geometry (or other possible geometries) with a diameter configured to be just larger than the diameter of a standard size of a stabilization wire 126 (e.g., k-wire, olive wire, etc.). In performing a Lapidus arthroplasty procedure, a physician may insert the stabilization wire 126 at least partially into the first metatarsal 204, where the stabilization wire 126 extends into and through the actuator 124. The actuator 124 may include a texture material or surface friction element on at least a portion of an outer surface thereof such that the actuator 124 may be gripped by a physician and, while the stabilization wire 126 is releasably coupled with the first metatarsal 204 via the actuator 124, manipulate the actuator 124 (and/or the stabilization wire 126) to as to derotate the first metatarsal 204. In performing such a derotation, the physician may manipulate the actuator 124 within the slot 122 from a more distal portion of the slot 122 to a more proximal portion of the slot 122 (where the distal and proximal portions of the slot are relative to distal and proximal portions of the curved member 120). In some aspects, the actuator 124 may include one or more threaded portions such that the actuator 124 may be assembled and disassembled into multiple components (and/or to facilitate coupling/decoupling with the slot 122 of the curved member 120).

The retention element 130 (which is described in greater detail subsequently with reference to FIG. 12) is shown to be arranged opposite the clamp 110 from the curved member 120 and, more specifically, opposite the shaft 144 of the coupling member 140. The coupling member is shown to include a knob 142 disposed opposite the coupling member from the distal-most portion of the shaft 144. Further, the knob 142 may include a texture or gripping element on the outer surface thereof to facilitate gripping and manipulation of the coupling member 140. The coupling member 140, at a position adjacent the knob 142 and at a proximal-most portion of the shaft 144 (where, as shown, the shaft 144 does not include the threading 139), is shown to be releasably (e.g., rotatably) coupled with a connecting member 150. The connecting member includes a first opening 152 on an upper portion thereof that incudes a substantially cylindrical geometry. As shown, the first opening 152 has a diameter larger than that of at least the proximal-most end of the shaft 144 adjacent the knob 142 such that at least a portion of the shaft 144 may be received within the connecting member 150. In some aspects, the connecting member 150 may be retained about the shaft 144 at the proximal-most end of the shaft 144. In some aspects, the knob 142 may be releasably couplable with the proximal-most end of the shaft 144 (e.g., via a threading).

The connecting member 150 is further shown to include a second opening 154 disposed at an opposite end of the connecting member 150 from the first opening 152. As shown, the second opening has a circular geometry similar in shape and size to that of the first opening 152, although in some aspects the geometry and/or size of the two openings may vary from one another. In some aspects, the first opening 152 may be positioned on the connecting member 150 at a different height than the second member 154. Similarly, the first opening 152 may be positioned such that a longitudinal axis extending therethrough would fall in a plane perpendicular to that in which a similar longitudinal axis of the second opening 154 would fall.

The second opening 154 is shown to facilitate releasable coupling with the retention element 130. The retention element 130 is shown to include a pair of projections 132 at a distal portion thereof, and a shaft 138 at a proximal portion thereof. The pair of projections 132 are configured to releasable couple with the second metatarsal 206. In some aspects, the shaft may include a threading along at least a portion thereof. The pair of projections 132 are shown to include various lateral dimensions along the length thereof where said lateral dimensions increase from the proximal to distal end of the pair of projections 132. At a point along the length of the pair of projections 132, the lateral dimension becomes greater than that of the second opening 152 such that the remaining length of the pair of protrusions between said lateral dimension becoming greater than that of the second opening 154 and the terminal end are retained below the second opening 154 unless a force is applied to move the retention element 130 in an upward direction (such that the outer surface of the pair of projections 132 contacts the outer edge of the second opening 154, thus biasing each of the pair of projections 132 toward one another and decreasing the lateral dimension, resulting in permitting a greater portion of each of the pair of projections be received into and/or through the second opening 154).

Manipulation of the knob 142 of the coupling member 140 may be configured to adjust the distance between the knob 142 and the coupling portion of the curved member 120. For example, rotation of the knob 142 may drive rotation of the shaft 144 such that the threading 146 travels into and through corresponding threads of the coupling member, thus positioning the curved member 120 nearer the knob 142 (e.g., collapsing the clamp 110). Similarly, the knob 142 may be actuated in an opposite manner to position the curved member 120 further from the knob 142 (e.g., expanding the clamp 110). For example, manipulating the knob 142 to collapse the clamp 110 may manipulate the curved member 120 and the retention element 130 closer to one another, thus closing the IM angle between the first and second metatarsals 204, 206, with most if not all of this movement being repositioning of the first metatarsal 204 relative to the second metatarsal 206.

The retention element 130 is shown to be received by, in order from inferior (lowest) to superior (highest): the second opening 154, a first threaded knob configured to engage with a threading 139 of the retention element to retain the retention element 130 within the second opening 154 (and compress/bias the pair of projections 132 toward each other), an alignment bar 170, and a second threaded knob configured to engage with the threading 139 to retain the alignment bar on the shaft 138 of the retention element 130 (and in a desired orientation).

The alignment bar 170 is shown to be a component of an alignment system 160, wherein the alignment system 160 is configured to be releasably coupled with the clamp 110 via the connecting member 150. The alignment bar 170 is shown to include an opening 172 having a substantially cylindrical geometry (although other geometries may be found in other embodiments) with a lateral dimension greater than that of the shaft 138 of the retention element 130, but lesser than that of the first and second knobs disposed directly below and above the alignment bar 170 (specifically directly above and below the opening). In some aspects, the opening may be the same as and/or similar to those of the connecting member 150. The opening, as mentioned previously, is configured to receive at least a portion of the shaft 138 of the retention element 130. In some aspects, the interior surface of the opening may include a threading complimentary to that of the threading 139 such that said threading would engage and releasably (e.g., threadably) couple the alignment bar 170 with the retention element 130.

The alignment bar 170 is shown to include an opening 172 that is configured as an elongated geometry defined by a pair of parallel sides forming the longest dimension thereof and a pair of rounded edges defining the shortest dimension thereof. Disposed within the opening 172 is a pin 174 configured to be received at least partially therein/there-through by a bore extending through the alignment bar vertically, where said bore spans the opening 172. Accordingly, the pin 174 is removable from the alignment bar. The opening 172 is shown to include a substantially circular portion at a first end thereof having a greater lateral dimension than that of the remainder of the opening 172, which is separated from the remainder of the opening 172 by the pin 174. The circular portion may be configured to accommodate at least a portion of a slider 176 therein, wherein the slider has a substantially circular cross-section and/or cylindrical geometry with said cross-section having a dimension lesser than that of the circular portion of the opening 172. The slider 176 may also include first and second portions having a greater lateral dimension than that of the opening 172 (excluding the circular portion), with said first and second portions positioned opposite an intermediate portion having a lateral dimension lesser than that of the opening 172 (again, excluding the circular portion). Accordingly, the pin 174 may be removed from the guide arm 170, the slider inserted in the opening within the circular portion, the slider manipulated (e.g., translated, slid, etc.) within the opening 172 such that the pin 174 may be replaced between the circular portion and the slider 176. The slider 176 may thus be retained within the opening 172 between the pin 174 and the end of the opening opposite the circular portion.

The slider 176 is shown to include an opening 178 extending therethrough and, when the slider is positioned within the opening 172 of the guide arm 170, establishing fluid communication from one side of the guide arm 170 to another opposite side via (e.g., through) the slider 176. As shown in FIGS. 1-7, the slider opening 178 includes a substantially rectangular cross-sectional geometry, although in some embodiments the opening 178 may include alternate geometries (e.g., cylindrical, etc.). The opening 178 is shown to receive an extension 180, where the extension 180 includes a shaft 182 having a cross-sectional geometry complimentary to that of the opening 178, but with a smaller lateral dimension to accommodate the insertion of the shaft 182 into the opening 178 and movement (e.g., translation) of the shaft 182 at least partially therethrough. The shaft 182 is shown to have a substantially linear geometry (e.g., the shaft, despite having a square/rectangular cross-sectional geometry, is positioned about a longitudinal axis). When positioned within the slider 176, the extension 180 is shown to be substantially perpendicular to a longitudinal axis of the alignment bar 170 (with the alignment bar, subsequently, approximately perpendicular to the coupling member 140, and thus approximately parallel with the extension 180). In some aspects, the alignment bar 170 may be manipulated such that it is positioned directly above and in a plane substantially parallel to the intramedullary axis of the second metatarsal 206.

The extension 180 is shown to include a head 184 positioned at an end of the shaft 182 opposite that shown to have been inserted into and received by the opening 180. As shown, the head 184 includes a geometry and a lateral dimension different than and greater than, respectively, that of the opening 178 of the slider 176. Accordingly, the head 184 may act as a mechanical stop to limit the insertion depth of the shaft 182 of the extension 180 within the opening 178. The head 184 is shown to include a male dovetail component 186.

The alignment system 160 is further shown to include a wire guide 190 including a dovetail 191, where the dovetail 191 is a female dovetail component and releasably (and slidably) couplable with the male dovetail component 186 of the extension 180. Accordingly, the extension 180 and the wire guide 190 are couplable via the dovetail components 186 and 191. In some aspects, the male and female configuration of the dovetail components 186, 191 may be reversed. The wire guide 190 is further shown to include an upper portion 192 (which includes the dovetail 191) and a base 197, where the upper portion 192 and the base 197 are separated by a shaft 196. In some aspects, the upper portion 192 includes a substantially hemispherical lobe extending approximately orthogonally from the upper portion 192.

The upper portion 192 is further shown to include a measurement guide 193 extending laterally from the wire guide 190. In some aspects, the measurement guide 193 may be releasably couplable with the wire guide 190 at the upper portion 192 thereof. A measurement bar 194 may also be coupled with the wire guide 190 via an opening disposed on the shaft 196 thereof. The measurement bar 194 is shown to be positioned below the measurement guide 193 such that at least a portion of the measurement bar 194 may be visible through one of a plurality of apertures disposed at a distal end of and extending through the measurement guide 193. In some aspects, the measurement bar 194 may be positioned directly above an intramedullary axis of the first metatarsal 204 (e.g., in a plane parallel to the intramedullary axis of the first metatarsal 204) to assist a physician in visualizing the IM angle between the first and second metatarsals 204, 206 (shown between the alignment bar 170 and the measurement bar 194. In some aspects, the measurement guide 193 and the measurement bar 194 may couple with the dovetail 186 (e.g., where the dovetail 186 is a male dovetail and at least one of the measurement guide 193 and/or the measurement bar 195 includes a complimentary female dovetail) or may couple with the slider 176 rather than releasably coupling with the wire guide 190. For example, a first alignment apparatus including the measurement guide 193 and the measurement bar 194 may be coupled with the extension 180 and/or the alignment bar 170, one or more portions of the anatomy of the foot 200 and/or the system 100 may then be aligned, and then the measurement guide 193 and measurement bar 194 may be decoupled and replaced with the wire guide 190.

The shaft 196 is shown to include a substantially rectangular cross-sectional geometry along the length thereof, although the shaft 196 may include one or more alternative geometries in some embodiments. As shown, the shaft 196 includes a bend at an oblique angle (e.g., approximately 20-80 degrees) approximately two-thirds of the length of the shaft 196 from the upper portion and one-third of the length of the shaft 196 from the base 197. The aforementioned bend may be configured to accommodate a desired position of the upper portion substantially above a portion of the foot 200 (e.g., the medial cuneiform 202) and a desired position of the base 197 adjacent a medial or dorsal-medial surface of the medial cuneiform 202. The base 197 is shown to include a lobe extending laterally therefrom which, as shown in FIGS. 1-7, extends anteriorly relative to the foot 200. The aforementioned lobe is configured to include a hole 198 extending from a top surface of the lobe through to a bottom surface of the lobe such that a stabilization wire (e.g., the stabilization wire 126) may be inserted through the hole 198 and into the medial cuneiform 202. One or more geometric features/properties/components of the wire guide 190 may be configured to position the hole 198 at a desired dorsal-medial portion of the cuneiform 202 such that said stabilization wire may be inserted therethrough and the wire guide 190 decoupled from the extension 180. The base 197 is also shown to include a fin 199 extending from a bottom surface thereof at a side of the base portion 197 opposite the lobe. The fin 199 may extend from the bottom surface of the base portion 197 at a substantially perpendicular angle, and may be configured to be inserted in the joint space of the Lapidus joint (e.g., between the medial cuneiform 202 and the first metatarsal 204) so as to guide positioning of the wire guide 190 and components thereof (e.g., the hole 198, etc.).

Referring now to FIG. 7, an alternate embodiment of the system 100 is shown, according to the present disclosure. The components of the system 100 as shown in FIG. 7 do not differ from those of the system 100 shown in FIGS. 1-6, with one exception. As shown in FIG. 7, the curved member 120 is absent and a curved member 320 has replaced the curved member 120. The curved member 320 is shown to include a coupling portion at a first (e.g., proximal) end, wherein said coupling portion is configured to receive at least a portion of a shaft 144 of the coupling member 140. As shown, the shaft 144 includes a threading 146 disposed along at least a portion of the length thereof. The coupling portion of the curved member 320 is shown to include a substantially cylindrical geometry with an open center portion extending therethrough about a central longitudinal axis. In some aspects, the inner surface of said open center portion may include a threading complimentary to the threading 146 of the shaft 144 of the coupling member 140 such that the curved member 320 may releasably (and, for example, rotatably, threadedly, etc.) couple with at least a portion of the coupling member 140. The curved member 320 is shown to extend in a distal direction (e.g., opposite the coupling portion) in a curved geometry, where said curved geometry (which may include one or more radius/radii of curvature) is configured to contact an outer surface of the first metatarsal 204 (on a lateral side thereof). As shown, the curved member 320 has a substantially concave geometry on a first (e.g., medial-facing, as shown) side, and a substantially convex geometry on a second (e.g., lateral-facing, as shown) side. In some aspects, only a portion of the curved member 320 may contact the surface of the first metatarsal 204 at a time, with said curvature of the curved member 320 configured to facilitate smooth movement of the first metatarsal 204 along the curvature when manipulated by a physician. It should be noted that the curved member 320 does not include the slot 122 of the curved member 120. Accordingly, the curved member 320 may be desirable to substitute in the system 100 for physicians who do not want a stabilization wire or knob to manipulate (e.g., derotate) the first metatarsal 204.

Figure 8:
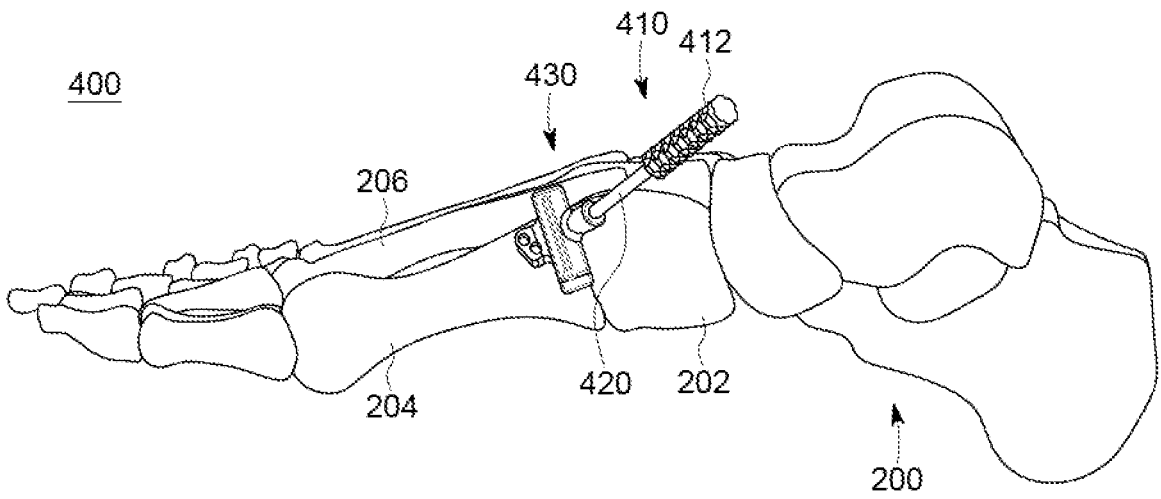
FIG. 8 is an elevated medial view of an instrument for implementation in conjunction with a system for performing a surgical procedure, in accordance with the present disclosure.
Figure 9:
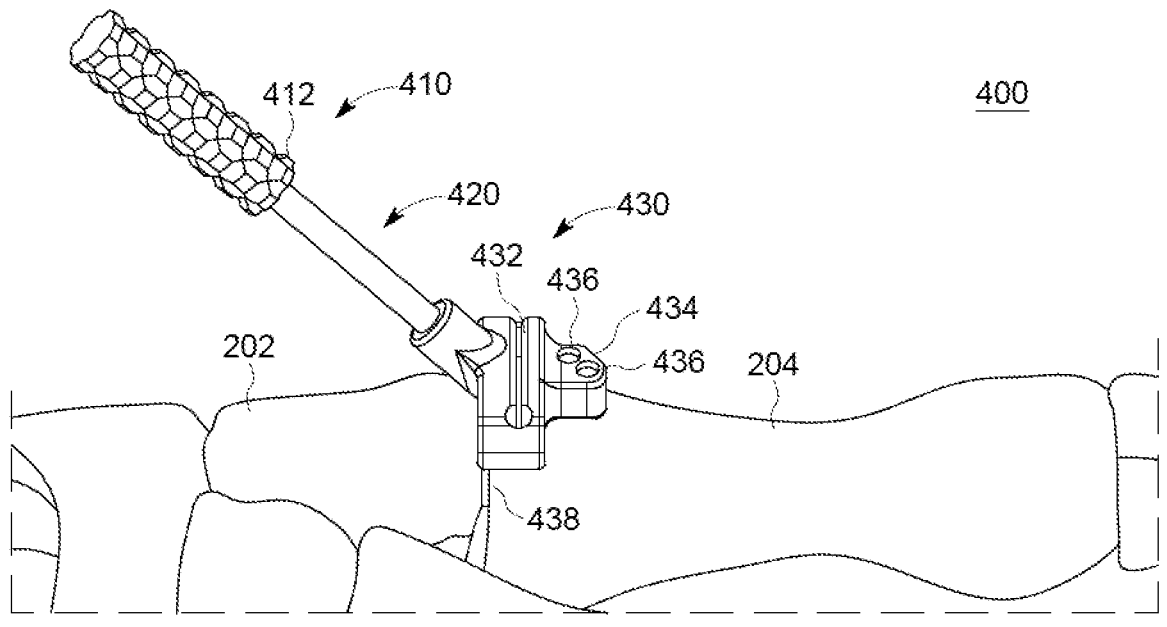
FIG. 9 is an elevated lateral view of the exemplary instrument of FIG. 8, in accordance with the present disclosure.

Referring now to FIGS. 8-9, an instrument 400 (e.g., a cut guide) is shown. In some aspects, the instrument 400 may be a component of the system 100 or may be a component of other systems for performing arthroplasty procedures. The instrument 400 is shown to include a handle 410 extending from a base 430, with a shaft 420 disposed between and integral with both the handle 410 and the base 430. The handle 410 is shown to include a textured surface 412 disposed circumferentially about the handle 410 which may facilitate a physician gripping the handle 410. The base 430 is shown to include a fin 438 extending from the bottom surface of the base 430 at a substantially perpendicular direction relative to the bottom surface of the base 430. The fin 438 is configured to be inserted into the joint space between the medial cuneiform 202 and the first metatarsal 204 (e.g., in the joint space of the Lapidus joint) such that the base portion is positioned adjacent to an outer surface (e.g., dorsal-medial) of the first metatarsal 204. The base 430 further includes a slot 432 disposed therein configured to accommodate a blade of a saw or other similar orthopedic cutting instrument such that a cut may be made to the first metatarsal 204 on an anterior/proximal portion thereof and the first metatarsal 204 may be prepared for fusion. The base 430 also includes a lateral projection 434 extending from the base 430, where the slot 432 is disposed between the lateral projection 434 and the interface of the base 430 and the shaft 420. The lateral projection 434 is shown to include at least one opening 436 sized to receive at least one stabilization wire therethrough and into the first metatarsal 204. One or more stabilization wires may be placed via the at least one opening 436 and, after a cut has been made via the slot 432, the instrument 400 may be removed while the stabilization wires remain in place (or are removed).

Figure 10:
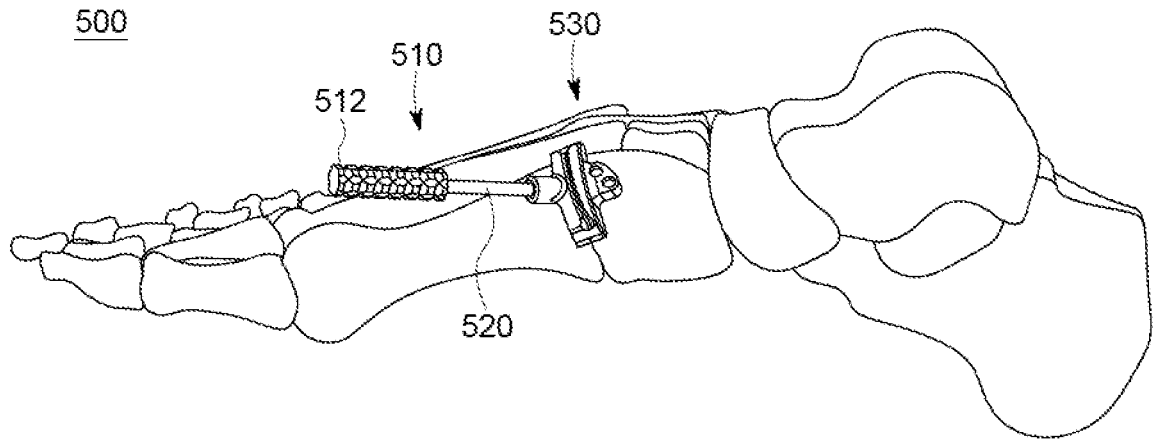
FIG. 10 is an elevated lateral view of an alternative instrument of the exemplary instrument of FIG. 8, in accordance with the present disclosure.
Figure 11:
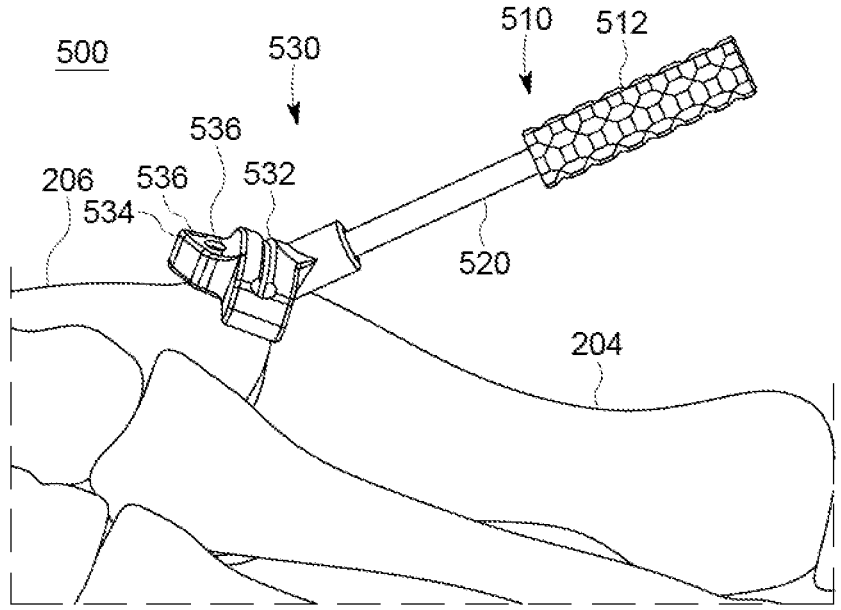
FIG. 11 is an elevated lateral view of the exemplary instrument of FIG. 10, in accordance with the present disclosure.

Referring now to FIGS. 10-11, an alternative instrument 500 (e.g., a cut guide) is shown. In some aspects, the instrument 500 may be a component of the system 100 or may be a component of other systems for performing arthroplasty procedures. The instrument 500 is shown to include a handle 510 extending from a base 530, with a shaft 520 disposed between and integral with both the handle 510 and the base 530. The handle 510 is shown to include a textured surface 512 disposed circumferentially about the handle 510 which may facilitate a physician gripping the handle 510. The base 530 is shown to include a fin 538 extending from the bottom surface of the base 530 and at a substantially perpendicular direction relative to the bottom surface of the base 530. The fin 538 is configured to be inserted into the joint space between the medial cuneiform 202 and the first metatarsal 204 (e.g., in the joint space of the Lapidus joint) such that the base portion is positioned adjacent to an outer surface (e.g., dorsal-medial) of the medial cuneiform 202. The base 530 further includes a slot 532 disposed therein that is configured to accommodate a blade of a saw or other similar orthopedic cutting instrument such that a cut may be made to the medial cuneiform 202 on an anterior/proximal portion thereof and the medial cunei-form 202 may be prepared for fusion. The base 530 also includes a lateral projection 534 extending from the base 530, where the slot 532 is disposed between the lateral projection 534 and the interface of the base 530 and the shaft 520. The lateral projection 534 is shown to include at least one opening 536 sized to receive at least one stabilization wire therethrough and into the medial cuneiform 202. One or more stabilization wires may be placed via the at least one opening 536 and, after a cut has been made via the slot 532, the instrument 500 may be removed while the stabilization wires remain in place (or are removed).

Figure 12:
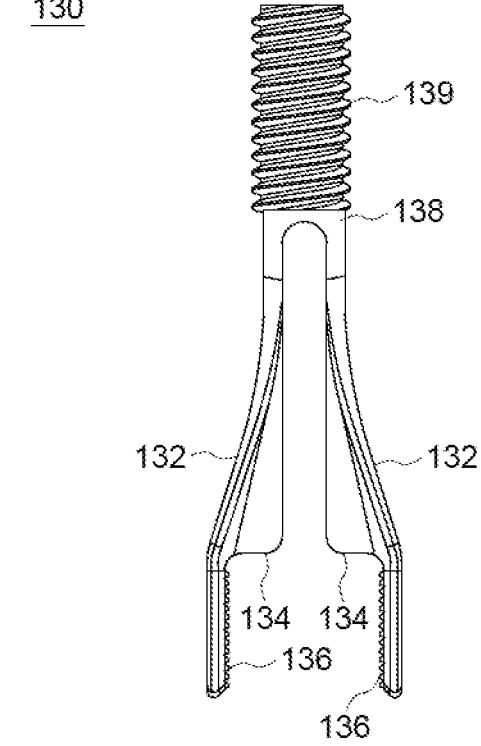
FIG. 12 is front view of an exemplary retention mechanism for implementation in performing a surgical procedure, in accordance with the present disclosure.

Referring now to FIG. 12, the retention element 130 (e.g., the metatarsal grip 130) is shown in a decoupled state from the clamp portion 110. The retention element 130 is shown to include a shaft 138 extending in a direction opposite (e.g., proximally, with the pair of projections 132 extending distally) the pair of projections 132. The shaft 138 is configured to be integral with each of the pair of projections 132 and, as shown in FIG. 12, has a substantially cylindrical geometry. The shaft 138 is shown to include circumferential threading 139 extending along the entirety of the shaft 138 (although in some embodiments, the threading 139 may extend along at least a portion of the shaft 138). Each of the pair of projections 130 is shown to extend from the shaft 138 at a substantially perpendicular angle (or lack of angle) along an interior portion thereof, and are further shown to extend from the shaft at a substantially oblique angle from one another along an exterior portion thereof (where said angles or lack of angles are based on an extended plane positioned on the surface of the interior portions and exterior portions of the projections 132, respectively). Each of the pair of projections 132, shown in FIG. 12 as a pair of prongs or other extension elements (protrusions, arms, etc.) extend from the shaft 138 adjacent to the distal-most portion of the threading 139.

As shown, each of the pair of projections 132 include a lobe 134 extending from the inner surface of each of the projections 132 such that a first portion of the lobe 134 includes a straight edge parallel to an opposing parallel edge of the opposing lobe 134 (e.g., substantially parallel to a longitudinal axis of the shaft 138). Similarly, each of the lobes 134 includes a second portion with a second straight edge substantially perpendicular to the first straight edge of each lobe 134. In some aspects, one or both of the lobes 134 may contact a superior (e.g., upper) portion of a metatarsal (e.g., the second metatarsal) such that the retention element 130 contacts the medial and lateral surfaces of the second metatarsal via the distal portion of the pair of projections 132, and the superior surface of the second metatarsal by at least a portion of one or both of the lobes 134. In some aspects, the lobes 134 may have alternate geometries, for example hemispherical or another alternative shape. Each projection 132 of the pair of projections 132 is shown to include a texture or surface configuration 136 disposed on an interior portion thereof and arranged distally relative to the pair of lobes 134. In some aspects, the texture or surface configuration 136 may be uniform on both of the pair of projections 132, or may vary from one single projection of the pair of projections 132 to the other. Further, the texture or surface projections 136 may be configured such that contact of the texture or surface projections 136 with the medial and lateral surfaces of the second metatarsal may create friction, thus increasing the retention of the second metatarsal between the pair of projections 132.

The system 100 shown and described previously herein may be implemented in conjunction with one or more surgical techniques to perform one or more bunion proce-dures (for example, a Lapidus arthrodesis). In performing such a procedure, a physician may implement the system 100 (which may omit one or more of the components shown and described herein, and/or may add additional components not shown and described herein) in performing a series of surgical steps (e.g., a surgical method) the same as or similar that described subsequently. Similarly, a physician may implement an alternative system to the system 100 that may or may not include one or more components of the system 100 in performing a procedure according to the subsequently described surgical method. That is to say that the surgical methodology described herein may be implemented in con-junctions with the system 100, but is not dependent on nor does it require the system 100. Accordingly, any references to the system 100 and/or components thereof in the descrip-tion of the surgical method should be understood as exem-plary, as other components that may be the same as and/or similar to those shown and described herein may also be implemented in conjunction with the surgical method.

A surgical method for performing a fusion procedure for the Lapidus joint of a patient may include a first step of creating a dorsal-medial incision in the skin adjacent the Lapidus joint. An instrument, for example the instrument 400, may be inserted into the incision such that a fin (e.g., the fin 438) is within the joint space between the medial cuneiform 202 and the first metatarsal 204. One or more stabilization wires may be inserted through openings in the instrument (e.g., the at least one opening 436) and coupled with the first metatarsal 204 to maintain the instrument in a desired position. A cut may then be made to the first metatarsal 204 via a slot (e.g., the slot 432) of the instrument. The instrument and stabilization wires may then be removed.

The surgical method may then include a second step of creating a stab incision lateral of the second metatarsal 206 of a patient (and preferably proximal/posterior from the head of the second metatarsal 206). Connective tissue may be cleared, and a retention element (e.g., the retention element 130) may be inserted and releasably coupled with the second metatarsal 206.

The surgical method may then include releasably coupling a connecting member (e.g., the connecting member 150) with the retention element. Such a connecting element may then be secured to the retention element via a threaded knob which is releasably coupled with the retention element such that it is positioned superior relative to the coupled portion of the connecting member. An alignment bar (e.g., the alignment bar 170) may then be coupled with the retention element at a position superior the first threaded knob, with a second threaded knob then coupled with the retention element superior to the coupled portion of the alignment bar to secure the alignment bar to the retention element.

The surgical method may further include coupling various components (e.g., the extension 180, the measurement guide 193, the measurement bar 194, etc.) directly or indirectly with the alignment bar. For example, a measurement guide may be releasably coupled with a wire guide which has been releasably coupled with an extension, which has been releasably coupled with the alignment bar (and/or components thereof). The measurement guide may be positioned over the Lapidus joint pointing distally, and may further be manipulated relative to an alignment bar with an angle between the two components then read by a physician.

The surgical method may further include a step of releasably coupling a wire guide (e.g., the wire guide 190) with the extension and/or the alignment bar such that a base of the wire guide is positioned adjacent the joint space and, more specifically, adjacent the medial cuneiform 202. The surgical method may further include inserting a stabilization wire through a hole in the base of the wire guide and releasably coupling said wire with the medial cuneiform 202. The wire guide and the extension may then be removed/decoupled.

The surgical method may further include the step of coupling an instrument for example the instrument 500, with the stabilization wire coupled with the medial cuneiform 202 such that a fin (e.g., the fin 538) is within the joint space between the medial cuneiform 202 and the first metatarsal 204. One or more stabilization wires may be inserted through openings in the instrument (e.g., the at least one opening 536) and coupled with the medial cuneiform 202 (potentially in addition to the exiting wire) to maintain the instrument in a desired position. A cut may then be made to the medial cuneiform 202 via a slot (e.g., the slot 532) in the instrument. Such a cut may be made perpendicular to the alignment bar. The instrument and stabilization wires may then be removed.

The surgical method may also include creating a stab incision on a medial side of the first metatarsal 204 (e.g., just proximal of the head of the first metatarsal 204). Further, a portion of a clamp (e.g., the clamp 110, the curved member 120, etc.) may be positioned adjacent and/or directly/indirectly coupled with the first metatarsal 204. The clamp may then be actuated so as to reduce an IM angle between the first and second metatarsals 204, 206 by manipulating a coupling member (e.g., the coupling member 140). The first metatarsal 204 may then be derotated via an actuator (e.g., the actuator 124) and/or a stabilization wire may be coupled with the first metatarsal 204 via the actuator. Such derotation may then be held in place by one or both of the actuator and/or the stabilization wire.

The surgical method may further include the step of dorsiflexing the first toe to activate the Windlass mechanism (e.g., compressing the Lapidus joint). One or more stabilization wires may then be coupled with the first metatarsal 204 and the medial cuneiform 202 in order to hold the Lapidus joint in a desired, corrected orientation. The remaining elements of the clamp and/or system may them be removed. A fixation element, for example a plate or intramedullary nail such as those incorporated by reference herein, may then be applied across the Lapidus joint to complete the desired arthroplasty (the surgical portion).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An alignment system, comprising:
   a clamp portion, comprising:
       a curved member configured to contact a medial portion of a first metatarsal of a patient;
       a retention element configured to releasably couple with a second metatarsal of the patient, wherein the retention element is arranged substantially opposite the clamp portion from the curved member and wherein the retention element comprises:
           a shaft; and a pair of projections extending from the shaft and terminating at a distal portion of the retention element; and a coupling member, comprising:

a shaft portion comprising a threading disposed on at least a portion of an outer surface thereof; and a knob disposed opposite the coupling member from a distal-most portion of the shaft portion, and wherein actuation of the knob of the coupling member is configured to translate the curved member along a length of the shaft portion of the coupling member;

an alignment portion releasably coupled with the clamp portion, comprising:

an alignment bar; and an extension coupled with the alignment bar and configured to releasably couple with a guide arm.

2. The alignment system of claim 1, wherein the curved member comprises a coupling portion configured to threadably and translatably couple with the shaft portion of the coupling member.

3. The alignment system of claim 1, wherein the clamp portion further comprises:

a connecting member comprising:

a first opening configured to receive at least a portion of the shaft portion of the coupling member therein; and a second opening configured to receive at least a portion of the shaft of the retention element therein.

4. The alignment system of claim 3, wherein the first opening comprises a first longitudinal axis and the second opening comprises a second longitudinal axis, wherein the first and second longitudinal axes are positioned in planes substantially orthogonal to one another.

5. The alignment system of claim 1, wherein translation of the curved member along the length of the shaft portion of the coupling member is configured to increase or decrease a distance between the retention element and the curved member.

6. The alignment system of claim 1, wherein the alignment bar comprises a first opening configured to receive at least a portion of the shaft of the retention element therethrough.

7. The alignment system of claim 6, wherein the alignment bar further comprises:

an elongated opening and a slider disposed within and translatable along a length of the elongated opening, wherein the slider comprises a bore extending therethrough.

8. The alignment system of claim 1, further comprising:

a guide portion comprising a shaft protruding from a lateral portion thereof and configured to be received at least partially therethrough a bore of a slider of the alignment bar.

9. A retention element, comprising:

a shaft; and a pair of projections extending from a distal-most point of the shaft, wherein the pair of projections extend substantially parallel to one another, wherein each of the projections further comprise:

a lobe disposed on an inner portion thereof and extending into a space between each of the projections and wherein each lobe of the pair of projections is spaced apart from the other lobe.

10. The retention element of claim 9, further comprising:

a threading disposed on at least a portion of the shaft.

11. The retention element of claim 10, wherein each lobe of the projections further comprise:

a first portion with a first straight edge parallel to an opposing parallel edge of the opposing lobe; and a second portion with a second straight edge substantially perpendicular to the first straight edge of each lobe.

12. The retention element of claim 11, wherein each of the projections further comprise:

a texture disposed on an inner portion thereof and positioned between the lobe and an end of the projection.

13. The retention element of claim 12, wherein each of the pair of projections define a space therebetween configured to receive at least a portion of a bony anatomy of a patient.

14. The retention element of claim 13, wherein each of the pair of projections are configured to be flexible such that a force applied simultaneously to an outer surface of each of the projections decreases the space between the projections.

15. The retention element of claim 12, wherein each of the projections are integral with the shaft.

16. A method of coupling an alignment system with the anatomy of a patient, comprising:

inserting a retention element comprising a pair of projections over a first bony anatomy of a patient such that the first bony anatomy is disposed at least partially between the projections;

releasably coupling a connecting member with the retention element such that at least a portion of a shaft of the retention element is received through a first opening of the connecting member;

releasably coupling the connecting member with a coupling member such that a shaft of the coupling member is received through a second opening of the connecting member;

releasably coupling a curved member with the shaft portion of the coupling member such that at least a portion of the shaft of the coupling member is received through a third opening of the curved member; and actuating the coupling member to adjust the space between the curved member and the retention element such that the curved member is positioned adjacent a second bony anatomy of the patient.

* * * * *